United States Patent
Chen et al.

(10) Patent No.: US 6,720,430 B2
(45) Date of Patent: Apr. 13, 2004

(54) MONOMER FOR CHEMICAL AMPLIFIED PHOTORESIST COMPOSITIONS

(75) Inventors: Chi-Sheng Chen, Sanchung (TW); Yen-Cheng Li, Sanchung (TW); Meng-Hsum Cheng, Chung-Li (TW)

(73) Assignee: Everlight USA, Inc., Pineville, NC (US)

( * ) Notice: Subject to any disclaimer, the term of this patent is extended or adjusted under 35 U.S.C. 154(b) by 41 days.

(21) Appl. No.: 10/154,797

(22) Filed: May 28, 2002

(65) Prior Publication Data

US 2003/0229234 A1 Dec. 11, 2003

(51) Int. Cl.$^7$ .................. C07D 333/74; C07D 307/00
(52) U.S. Cl. ............................. 549/45; 549/300
(58) Field of Search ................... 549/45, 300

(56) References Cited

U.S. PATENT DOCUMENTS

| 6,271,412 B1 | 8/2001 | Chang et al. | ........... 560/220 |
| 6,280,898 B1 | 8/2001 | Hasegawa et al. | ....... 430/270.1 |
| 6,316,159 B1 | 11/2001 | Chang et al. | ......... 430/270.1 |
| 6,579,659 B2 * | 6/2003 | Uetani et al. | ............ 430/270.1 |

OTHER PUBLICATIONS

Tsutsumi et al, CA138:18048, Nov., 2002.*

* cited by examiner

Primary Examiner—Deborah C Lambkin
(74) Attorney, Agent, or Firm—Bacon & Thomas

(57) ABSTRACT

The present invention discloses a compound having the following formula (I),

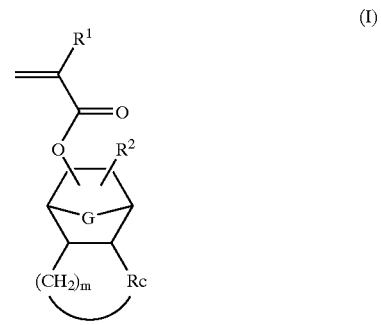

wherein $R^1$ is H, haloalkyl group or $C_1$–$C_4$ alkyl group; $R^2$ is hydroxyl group, $C_1$–$C_8$ alkoxy group or $C_1$–$C_8$ thioalkyl group; G is $(CH_2)_n$, O or S, wherein n is 0, 1, 2, 3 or 4; Rc is a lactone group; and m is 1, 2 or 3. This compound is a monomer and suitable for synthesis to form polymers with good hydrophilicity, adhesion and dry-etch resistance. Particularly, this compound can form photosensitive polymers or copolymers by reacting with suitable photosensitive monomers.

14 Claims, No Drawings

MONOMER FOR CHEMICAL AMPLIFIED PHOTORESIST COMPOSITIONS

FIELD OF THE INVENTION

The present invention relates to unsaturated polycyclic esters, and particularly to unsaturated polycyclic ester monomers, which are suitable for polymer synthesis producing polymers having good hydrophilicity, adhesion and dry-etch resistance.

BACKGROUND OF THE INVENTION

Integral circuit layering is crucial in semiconductor industries such that the number of integral layers on an integral circuit must be maximized. Therefore, narrower wire widths for lithography are required. To achieve better resolution, light sources with shorter wavelengths or exposure systems with larger numerical apertures are applied.

Recently, a polymer suitable for the 193 nm wavelength light source was developed, which is a copolymer formed by four kinds of monomers and named iBMA-MMA-tBMA-MMA (poly isobornyl methacrylate-methyl methacrylate-t-butyl methacrylate-methacrylic acid). The structure of this polymer is as follows:

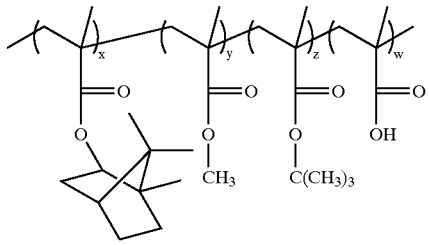

For such polymers, there are still some disadvantages, for example, low etch resistance and bad adhesion due to the four monomer composition. Therefore, if producing photoresist compositions with this polymer, creating a new process becomes necessary.

U.S. Pat. Nos. 6,271,412 and 6,280,898 and Japanese Patent Publication No. 2001-242627 have disclosed different monomers for synthesizing photosensitive polymers, which can form photoresist compositions and then be applied to semiconductor component manufacturing.

SUMMARY OF THE INVENTION

The object of the present invention is to provide unsaturated polycyclic ester monomers, which are suitable for synthesizing polymers having good hydrophilicity, adhesion and dry-etch resistance, or reacting with one or more unsaturated species to form polymers or copolymers.

The compound of the present invention has the following structure (formula I),

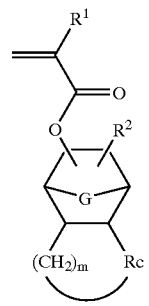

wherein $R^1$ is H, haloalkyl group or $C_1$–$C_4$ alkyl group; $R^2$ is hydroxyl group, $C_1$–$C_8$ alkoxy group or $C_1$–$C_8$ thioalkyl group; G is $(CH_2)_n$, O or S, wherein n is 0, 1, 2, 3 or 4; Rc is a lactone group; and m is 1, 2 or 3.

When a proper catalyst is added, formula (I) can form polymers or copolymers through polymerization or copolymerization with other vinyl monomers.

Furthermore, these polymers or copolymers can form chemical amplified photoresist compositions with photo-acid generators (PAG), additives and solvents. These compositions can then be applied to general lithography processes, and particularly to ArF, KrF or the like processes to obtain superior resolution, and photosensitivity.

DETAILED DESCRIPTION OF THE PREFERRED EMBODIMENTS

The present invention provides a compound of the formula (I),

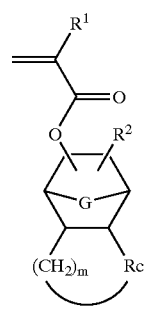

wherein $R^1$ is H, haloalkyl group or $C_1$–$C_4$ alkyl group; $R^2$ is hydroxyl group, $C_1$–$C_8$ alkoxy group or $C_1$–$C_8$ thioalkyl group; G is $(CH_2)_n$, O or S, wherein n is 0, 1, 2, 3 or 4; Rc is a lactone group; and m is 1, 2 or 3.

The formula (I) compound of the present invention can be synthesized by the following steps:

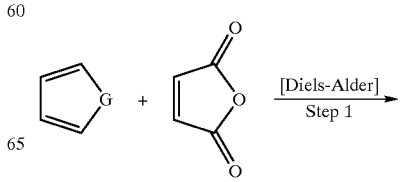

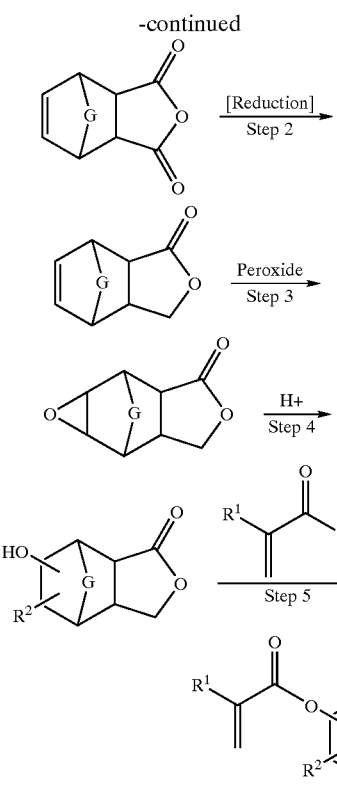

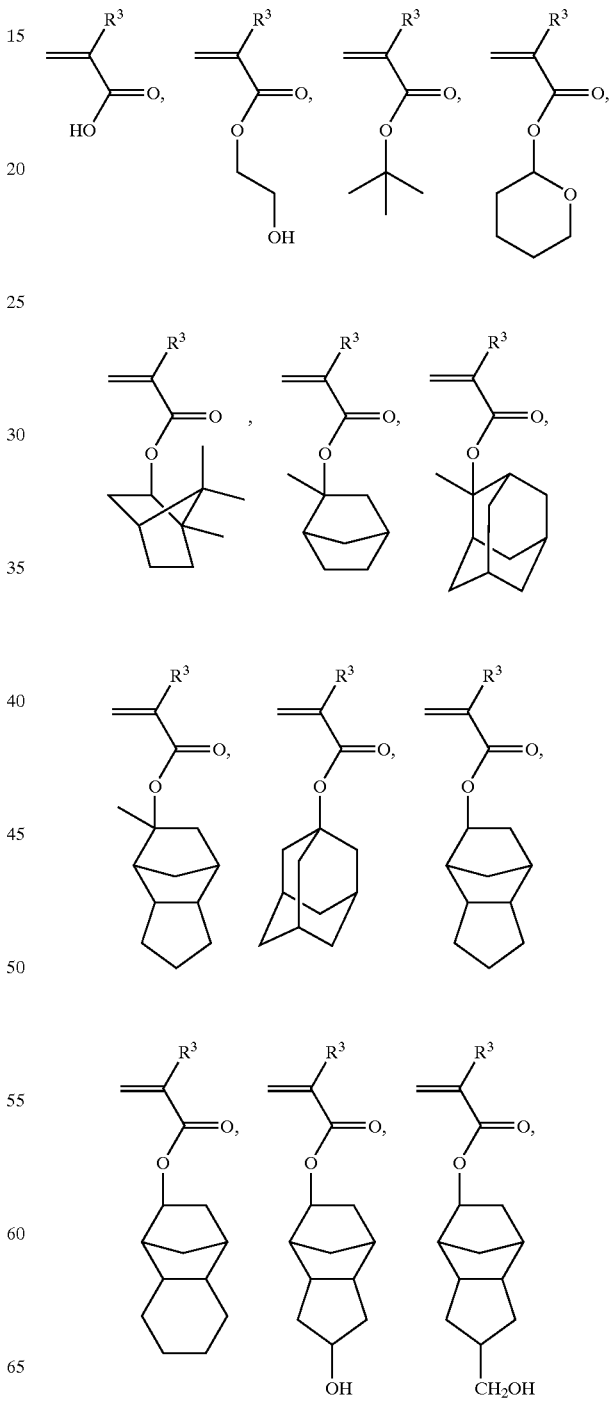

wherein $R^1$, $R^2$ and G are defined as the above.

In Step 1, a proper diene compound such as butadiene, cyclopentadiene, furan and thiophene, reacts with maleic anhydride to perform the Diels-Alder reaction. Then, the acid anhydride adducts are reduced under the well-known conditions in the second Step 2. Preferably reaction is carried out using sodium boron hydride in dried polar solvent such as dimethylformamide or tetrahydrofuran. In Step 3, peroxide is provided to oxidize the double-bond compound into an epoxide. In Step 4, the epoxide reacts with a proper nucleophilic reagent such as water, alcohol and thiol, to perform a ring opening addition reaction under an acidic environment obtaining a hydroxyl derivative. In Step 5, the hydroxyl derivative reacts with (alkyl)acryloyl chloride or acryloyl chloride to perform esterification resulting in the compound of formula (I). Detailed procedures for preparing the compound of the present invention are described in the preferred embodiments.

By polymerizing the compound of formula (I), polymers with repeated units can be obtained, which has the following structure formula (II),

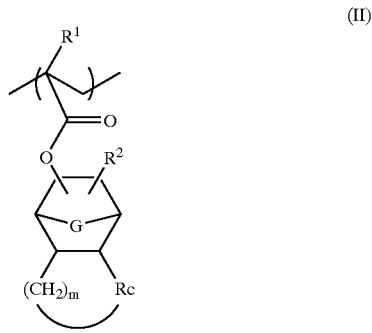

(II)

wherein $R^1$ is H, haloalkyl group or $C_1$–$C_4$ alkyl group; $R^2$ is hydroxyl group, $C_1$–$C_8$ alkoxy group or $C_1$–$C_8$ thioalkyl group; G is $(CH_2)_n$, O or S, wherein n is 0, 1, 2, 3 or 4; Rc is a lactone group; and m is 1, 2 or 3.

The compounds of formula (I) can be polymerized or copolymerized with other vinyl monomers to produce various polymers with or without the assistance of catalysts. Particularly, when applied to 193 nm processes, the vinyl monomers preferably have no aryl group to enable light to pass through. The following examples illustrate some of the vinyl monomers, wherein $R^3$ is H, haloalkyl group or $C_1$–$C_4$ alkyl group.

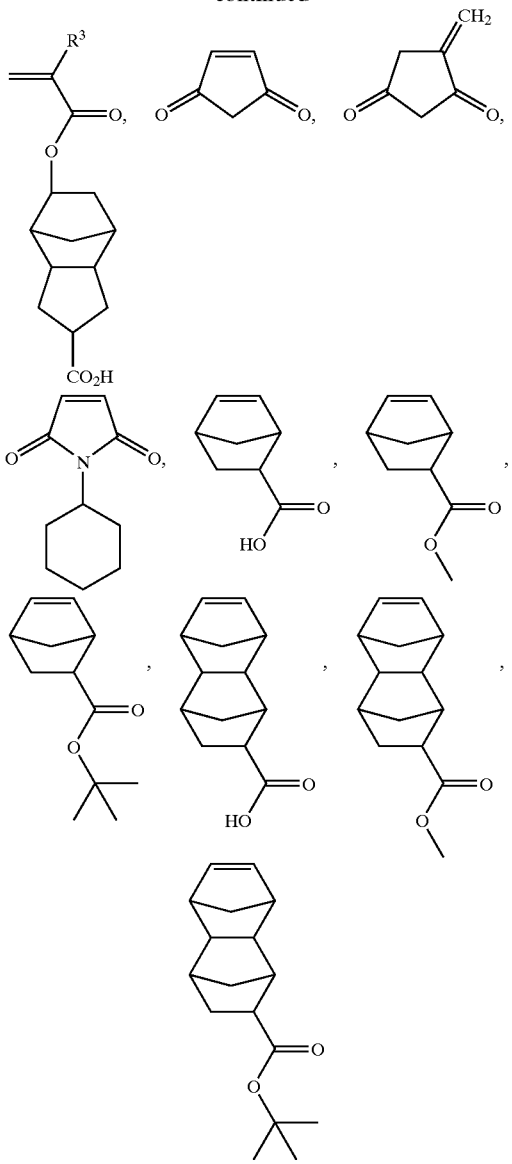

By reacting the compound, formula (I), with one or more of the above vinyl monomers, the polymers can be prepared. These polymers are suitable for producing chemically amplified photoresist compositions that can be applied to general lithography processes, and particularly to ArF, KrF or the like processes.

More detailed examples are used to illustrate the present invention, and these examples are used to explain the present invention. The examples below, which are given simply by way of illustration, must not be taken to limit the scope of the invention.

EXAMPLE 1
9-methoxy-5-oxo-4-oxa-tricyclo[5.2.1.0$^{2,6}$]dec-8-yl methacrylate (I-1)

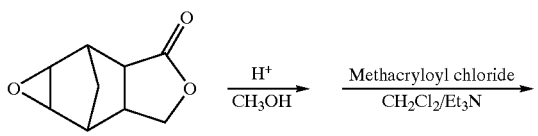

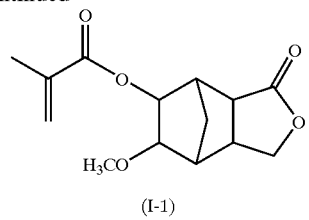

(I-1)

8,9-epoxy-3-oxo-4-oxa-tricyclo[5.2.1.0$^{2,6}$]decane (16.6 g) is dissolved in methanol (200 mL), and then reacts with concentrated sulfuric acid (0.25 mL) resulting in a ring opening reaction. After the reaction is completed, the solution is neutralized and concentrated in vacuum. The residue was dissolved in 200 ml of methylene chloride and 10.2 g of triethylamine. To this mixture below 15° C., 10.5 g of methacryloyl chloride was added dropwise. After the completion of addition, the solution was agitated for 4 hours at room temperature, followed by conventional extraction and washing. The oily substance collected was purified by silica gel column chromatography, yielding 18.4 g of 9-methoxy-5-oxo-4-oxa-tricyclo[5.2.1.0$^{2,6}$]dec-8-yl methacrylate) (I-1) (18.4 g), with a yield of 69%.

$^1$H-NMR (CDCl$_3$, 300 MHz) δ5.89 (1H, brs), 5.37 (1H, brs), 4.81 (1H, m), 3.96 (1H, m), 3.67–3.57 (2H, m), 3.54 (3H, s), 2.79 (1H, m), 2.57 (1H, m), 2.55 (1H, m), 2.37 (1H, m), 1.77–1.74 (4H, m), 1.38 (1H, m).

$^{13}$C-NMR (CDCl$_3$, 75 MHz) δ171.4, 165.6, 136.0, 124.8, 84.9, 79.5, 70.0, 51.0, 46.1, 45.7, 40.4, 39.1, 32.4, 17.8.

EXAMPLE 2
9-methoxy-5-oxo-4-oxa-tricyclo[5.2.1.0$^{2,6}$]dec-8-yl acrylate (I-2)

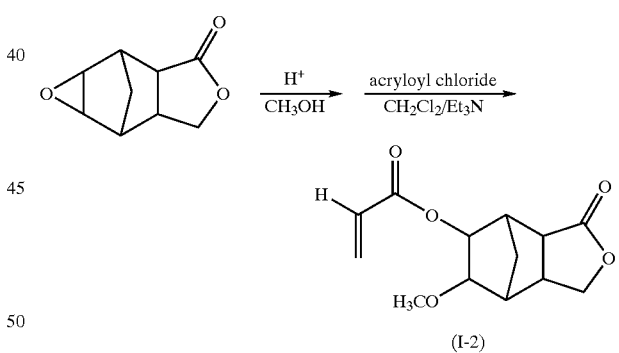

(I-2)

8,9-epoxy-3-oxo-4-oxa-tricyclo[5.2.1.0$^{2,6}$]decane (16.6 g) is dissolved in methanol (200 mL), and then reacts with concentrated sulfuric acid (0.25 mL) resulting in a ring opening reaction. Upon completion, the solution is neutralized and concentrated in vacuum. The residue was dissolved in 200 ml of methylene chloride and 10.2 g of triethylamine. To this mixture below 15° C., 10.5 g of methacryloyl chloride was added dropwise. After the completion of addition, the solution was agitated for 4 hours at room temperature, followed by conventional extraction and washing. The oily substance collected was purified by silica gel column chromatography, yielding 18.4 g of 9-methoxy-5-oxo-4-oxa-tricyclo[5.2.1.0$^{2,6}$]dec-8-yl acrylate) (I-1) (18.9 g), with a yield of 75%.

¹H-NMR (CDCl₃, 300 MHz, J in Hz) δ6.38 (1H, dd, J=17.4, 0.6), 6.11 (1H, dd, J=17.4, 10.5), 5.82 (1H, dd, J=10.5, 0.56), 5.01 (1H, brs), 4.17 (1H, d, J=5.0), 3.86 (1H, d, J=5.6), 3.79 (1H, dd, J=5.6, 2.7), 3.72(3H,s),2.95(1H,m), 2.81 (1H,m),2.73(1H,m),2.56(1H, brs), 1.95 (1H, d, J=10.9), 1.57 (1H, d, J=10.9).

¹³C-NMR(CDCl₃, 75 MHz) δ171.9, 165.0, 130.7, 128.6, 85.4, 80.0, 70.5, 51.6, 46.7, 46.2, 40.8, 39.6, 32.9.

EXAMPLE 3
4-ethoxy-9-oxo-8-oxa-bicyclo[4.3.0]non-3-yl acrylate) (I-3)

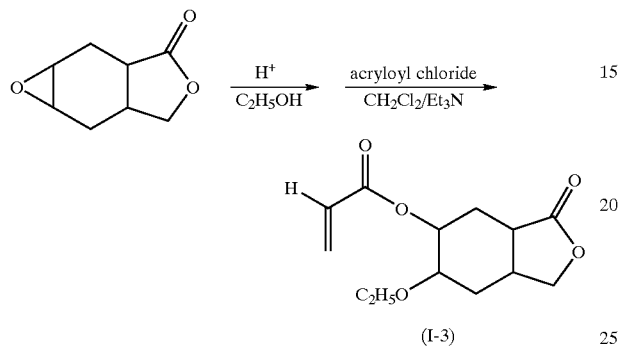

Repeat steps of Example 2, but replace the initial reactant 8,9-epoxy-3-oxo-4-oxa-tricyclo[5.2.1.0²·⁶]decane with 3,4-epoxy-7-oxo-8-oxa-bicyclo[4.3.0]nonane, and replace methanol with anhydrous ethanol. The colorless oil product, 4-ethoxy-9-oxo-8-oxa-bicyclo[4.3.0]non-3-yl acrylate (I-3), is obtained.

¹H-NMR (CDCl₃, 300 MHz, J in Hz) δ6.28 (1H, dd, J=17.4, 1.8), 5.99 (1H, dd, J=17.4, 10.6), 5.75 (1H, dd, J=10.6, 1.8), 4.91 (1H, brs), 4.11 (1H, m), 3.85 (1H, m), 3.58 (1H, m), 3.44 (1H, m), 3.22 (1H, m), 2.61–2.47 (2H, m), 2.25 (1H, m), 1.91–1.72 (2H, m), 1.09–0.97 (5H, m).

¹³C-NMR(CDCl₃, 75 MHz) δ171.6, 164.7, 130.9, 128.0, 71.2, 70.8, 69.2, 63.8, 35.7, 30.3, 25.1, 20.7, 14.9.

EXAMPLES 4–7

Repeat steps of Example 1, but replace the initial reactants and solvents with those listed in Table A. Table A also lists the products.

TABLE A

| | Initial Reactant | Solvent | Product |
|---|---|---|---|
| Example 4 | [epoxy tricyclic lactone structure] | 2-Propanol | I-4 [isopropoxy methacrylate tricyclic lactone structure] |
| Example 5 | [epoxy tricyclic lactone structure] | Cyclohexanethiol | I-5 [cyclohexylthio methacrylate tricyclic lactone structure] |

TABLE A-continued

| | Initial Reactant | Solvent | Product |
|---|---|---|---|
| Example 6 | | H₂O, THF | I-6 |
| Example 7 | | Methanol | I-7 |

APPLICATION EXAMPLE 1

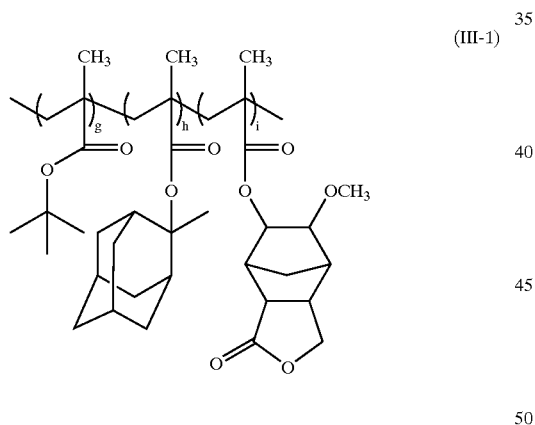

(III-1)

wherein g+h+i=1

Tetrahydrofuran (20 mL), tert-butyl methacrylate (2.13 g), 2-methyl-2-adamantyl methacrylate (4.69 g) and 9-methoxy-5-oxo-4-oxa-tricyclo[5.2.1.0$^{2,6}$]dec-8-yl methacrylate (3.99 g) are mixed in a reactor, and then an initiator 2,2'-azo-bis-isobutyronitrile (AIBN) (1.1 g) is added therein to perform the reaction at 65° C. After the reaction is completed, the solution to which tetrahydrofuran (20 mL) is added is transferred into a container containing hexane (1L) to generate white precipitate. The precipitate is then dried by filtration to obtain white powders (8.43 g), i.e., the formula (III-1) polymer. The yield is 78%. Weight-average molecular weight of the polymer measured with GPC is 14,100, and the glass transition temperature (Tg) is 169° C.

APPLICATION EXAMPLE 2

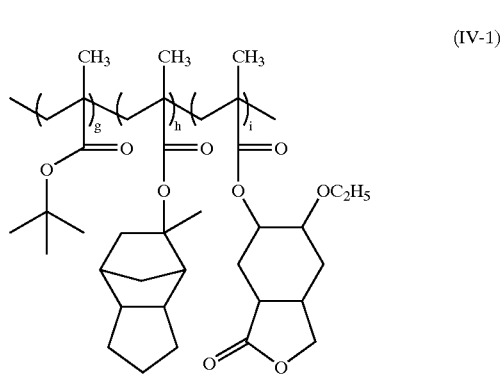

(IV-1)

wherein g+h+i=1

Tetrahydrofuran (20 mL), tert-butyl methacrylate (2.13 g), 2-methyl-2-adamantyl methacrylate (4.69 g) and 4-ethoxy-9-oxo-8-oxa-bicyclo[4.3.0]non-3-yl methacrylate (4.02 g) are mixed in a reactor. Next, an initiator 2,2'-azo-bis-isobutyronitrile (AIBN) (1.1 g) is added to perform an overnight reaction at 70° C., subsequently tetrahydrofuran (20 mL) is added therein. Next, the solution is transferred into a container containing hexane (1L) to generate white precipitate. The precipitate is then dried by filtration to obtain white powders (6.83 g), i.e., the formula (IV-1) polymer. The yield is 63%. Weight-average molecular weight of the polymer measured with GPC is 19,200, and glass transition temperature (Tg) is 121° C.

APPLICATION EXAMPLE 3
Preparing a Photoresist Composition

The polymer of formula (III-1) (2 g) obtained from Application Example 1, triphenylsulfonium perfluoro-1-butanesulfonate (TPS-PFBS) (0.05 g), tert-butyl cholate (TBC) (0.06 g), propylene glycol monomethyl ether acetate (PGMEA) (10.4 g) and N-(hydroxy methyl)piperidine (0.5 mg) are mixed well and then filtered through a 0.45 μm filter. The filtrate is then spread on a dry silicon piece by spinning to form a thin film.

The thin film is then dried at 130° C. for 90 seconds to obtain a 317.6 nm thick film. Next, the film is exposed to a DUV light source with a 193 nm wavelength and 15–35 mj/cm$^2$, and then heated on a thermoplate at 130° C. for 90 seconds.

Next, the film is developed with tetramethyl ammonium hydroxide (TMAH) aqueous solution (2.38%), and then washed with deionized water, and spin-dried. The exposed area shows a structure of resolution of 0.15 m under the observation of scanning electronic microscopy (SEM).

These photoresist compositions produced by the compound of the present invention can be applied to general lithography processes, and particularly to ArF, KrF or the like process to obtain superior resolution, and photosensitivity.

From the foregoing description, one skilled in the art can easily ascertain the essential characteristics of this invention, and without departing from the scope thereof, can make various changes and modifications of the invention to adapt it to various usages and conditions. Thus, other embodiments are also within the claims.

What is claimed is:

1. A compound of the following formula (I),

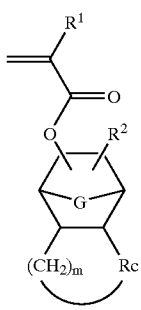
(I)

wherein:
$R^1$ is H, haloalkyl group or C1–C4 alkyl group;
$R^2$ is hydroxyl, $C_1$–$C_8$ alkoxy group or $C_1$–$C_8$ thioalkyl group;
G is $(CH_2)_n$, O or S, wherein n is 0, 1, 2, 3 or 4;
Rc is a lactone group; and
m is 1, 2 or 3.

2. The compound of claim 1, wherein said $R^1$ is H or a methyl group.

3. The compound of claim 1, wherein said $R^2$ is hydroxyl, $C_1$–$C_4$ alkoxy group or thioalkyl group.

4. The compound of claim 1, wherein said m is 1.

5. The compound of claim 1, wherein said G is $(CH_2)_n$, n is 0, 1 or 2.

6. The compound of claim 1, wherein said G is O or S.

7. The compound of claim 1, which is a compound of the following formula (I-1),

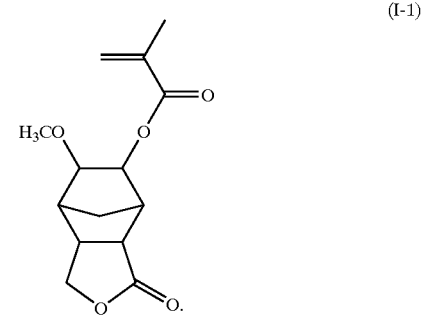
(I-1)

8. The compound of claim 1, which is a compound of the following formula (I-2),

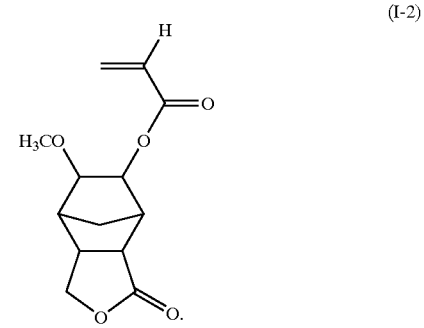
(I-2)

9. The compound of claim 1, which is a compound of the following formula (I-3),

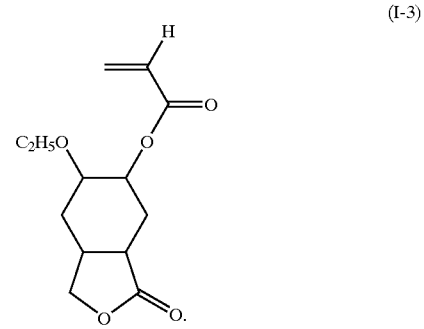
(I-3)

10. The compound of claim 1, which is a compound of the following formula (I-4),
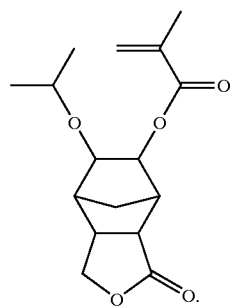
(I-4)
11. The compound of claim 1, which is a compound of the following formula (I-5),
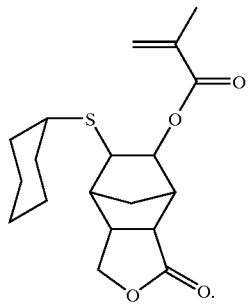
(I-5)
12. The compound of claim 1, which is a compound of the following formula (I-6),
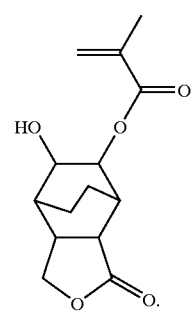
(I-6)
13. The compound of claim 1, which is a compound of the following formula (I-7),
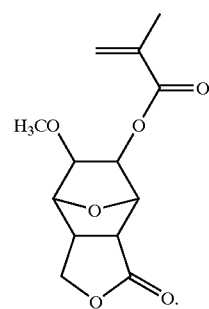
(I-7)
14. The compound of claim 5, wherein m is 1.
* * * * *